United States Patent [19]

Labaw et al.

[11] 4,321,393

[45] Mar. 23, 1982

[54] METHOD FOR PREPARING 2-CYANAMIDOBENZIMIDAZOLES OR 2-CYANAMIDOBENZOXAZOLES

[75] Inventors: Clifford S. Labaw, Philadelphia; Robert L. Webb, West Chester, both of Pa.

[73] Assignee: SmithKline Corporation, Philadephia, Pa.

[21] Appl. No.: 224,780

[22] Filed: Jan. 14, 1981

Related U.S. Application Data

[62] Division of Ser. No. 117,158, Jan. 31, 1980, Pat. No. 4,285,878.

[51] Int. Cl.$^3$ .............................................. C07D 235/04

[52] U.S. Cl. .................................... 548/222; 548/329; 548/306

[58] Field of Search ...................... 548/329, 222, 306

[56] References Cited

U.S. PATENT DOCUMENTS

4,142,886 3/1979 Hunter et al. ...................... 548/329

*Primary Examiner*—Henry R. Jiles
*Assistant Examiner*—Robert C. Whittenbaugh
*Attorney, Agent, or Firm*—William H. Edgerton; Richard D. Foggio; Alan D. Lourie

[57] ABSTRACT

A method of preparing 2-cyanamidobenzimidazoles or 2-cyanamidobenzoxazoles comprising reacting N-cyanodiphenoxyiminocarbonate with an o-amino or o-hydroxy aniline.

2 Claims, No Drawings

METHOD FOR PREPARING 2-CYANAMIDOBENZIMIDAZOLES OR 2-CYANAMIDOBENZOXAZOLES

This is a divisional application of Ser. No. 117,158 filed Jan. 31, 1980, now U.S. Pat. No. 4,285,878.

This invention relates to a new series of chemical intermediates which are N-phenyl-N'-cyano-O-phenylisoureas as well as methods for preparing and using them. The compounds of this invention are represented by the following structural formula:

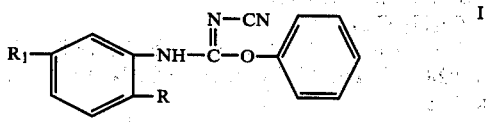

in which:

R is amino or hydroxy; and $R_1$ is hydrogen, halo such as fluoro, bromo, iodo or chloro, lower alkyl of 1-6 carbons such as methyl, ethyl or n-butyl, lower alkoxy of 1-6 carbons such as methoxy or propoxy, lower alkyl thio of 1-6 carbons such as methylthio or n-propylthio, lower alkyl sulfinyl of 1-6 carbons such as n-propylsulfinyl, phenylthio, phenyloxy, phenylsulfinyl, cyclohexylthio, cyclohexyloxy, cyclohexylsulfinyl, acetyl or thienylcarbonyl.

A subgenus of this invention are those compounds of Formula I in which R is amino and $R_1$ is propylthio, n-butyl, phenylthio, phenylsulfinyl or n-propoxy.

The compounds of this invention are prepared by the following route.

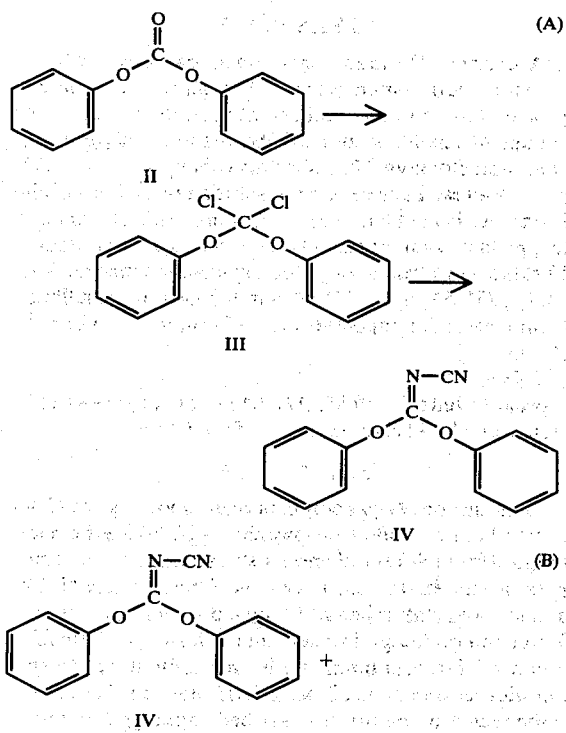

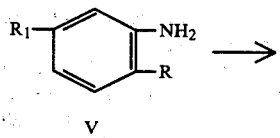

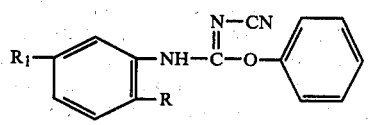

R and $R_1$ are as defined for Formula I.

The starting material, N-cyanodiphenoxyimidocarbonate (IV) is prepared according to reaction sequence A above, that is, by reacting diphenylcarbonate (II) with phosphorus pentachloride at 150°–160° to form 1,1-dichloro-1,1-diphenoxymethane (III) which is, in turn, reacted with cyanamide in an inert organic solvent at temperatures below 80° preferably at room temperature.

The N-cyanodiphenoxyimidocarbonate (IV) is then reacted in reaction sequence B above, that is, with a substituted o-phenylenediamine or o-aminophenol (V) to form the compounds of this invention. The reaction is run using about equimolar quantities of the two reactants in an organic solvent in which the reactants are soluble and which is inert under the reaction conditions such as preferably a lower alkanol such as methanol, ethanol or isopropanol. Alternatively, tetrahydrofuran, acetonitrile, ethyl acetate, butyl acetate, dimethylformamide, dimethylacetamide or dimethylsulfoxide may also be used as solvents.

The reaction is run until complete at about room temperature or below such as down to 0° for a short time such as from ¼ to 2 hours but at times up 12–24 hours. The progress of the reaction may be followed by analytical methods commonly used in the art such as gas chromatography or paper strip chromography. This reaction is also an object of this invention.

More strenuous reaction conditions such as temperatures at above room temperature may cause in situ cyclization of the intermediates of this invention to form the 2-cyanamidobenzimidazole or benzoxazoles of the formula:

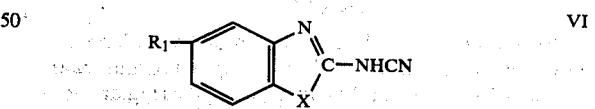

in which $R_1$ is as defined above for Formula I and X is oxy (—O—) or aza (—NH—).

Those skilled in the art may not wish to isolate the N-phenyl-N'-cyano-O-phenylisoureas of Formula I but continue the reaction to cyclize the isoureas of this invention by condensing out the second mole of phenol to form the 2-cyanamidobenzimidazole or benzoxazole of Formula VI. This reaction proceeds very readily at the reflux temperature of the reaction mixture especially if the reaction solvent boils below 100° or from 80°–100° if the solvent is of a higher boiling nature.

The compounds of Formula VI have utility per se for example see U.K. Pat. No. 1,408,408 or German Pat. No. 2,257,312 however they are of prime utility as chemical intermediates. Heating them at reflux in methanolic hydrogen chloride gives the corresponding anthelmintic 2-carbomethoxyaminobenzimidazoles or 2-carbomethoxyamino benzoxazoles.

The optionally substituted o-phenylenediamines and o-aminophenols of Formula V are known to the art, for example U.S. Pat. Nos. 3,682,952; 3,657,267; 4,026,938; 3,969,526 or 4,002,640; French Pat. No. 2,202,880.

The following illustrative examples are intended to teach those skilled in the art the practice of this invention but not to limit the invention described herebefore. All temperatures are Centigrade.

PREPARATION A

Diphenyl carbonate (1.0 kg, 4.67 mole) was melted and heated to 150°. Phosphorous pentachloride (1.1 kg, 5.36 mole) was added in portions so that the pot temperature remained above 110°. The reaction was heated to 160° and held at this temperature for 24 hours while phosphorous oxychloride was distilled off. After 24 hours the pot temperature was raised to 200° and held for 15 minutes. The reaction was cooled. Excess phosphorous oxychloride and pentachloride was removed by distillation under aspirator vacuum. The remaining liquid was distilled, bp 125–135/1 mm, and yielded 1.2 kg (96%) of 1,1-dichloro-1,1-diphenoxymethane (III) which assayed 85% by gas chromatography. This material was pure enough for subsequent use. A sample was redistilled to give a white solid after cooling, mp 42°–44°.

A solution of cyanamide (165 g., 3.9 mole) in 600 ml. of ethyl acetate was added to a solution of 1,1-dichloro-1,1-diphenoxymethane (467 g., 1.75 mole) in ethyl acetate (600 ml.) at such a rate that the temperature did not rise above 80°. After stirring for 3½ hours at room temperature, the precipitate was separated by filtration and washed with ethyl acetate (200 ml.). The solid was air-dried overnight then slurried with 2 l. of water. Solid sodium carbonate was added to adjust the ph to between 7.5 and 8.0. The suspension was filtered and washed with water. After vacuum drying, 378 g. of N-cyanodiphenoxyimidocarbonate, (91%) mp 156°–158°, was obtained.

Ir (nujol); 2140 cm$^{-1}$ (C≡N), 1670 cm$^{-1}$ (C≡N): $^1$H nmr (deuterochloroform); δ 7.0–7.6 (m, aromatics).

$C_{14}H_{10}N_2O_2$

Anal. Calcd: C, 70.58; H, 4.23; N, 11.76; M+238 Found: C, 70.36; H, 4.23; N, 11.83; M+238.

EXAMPLE 1

Phenylenediamine (2.16 g., 0.02 mole) was dissolved in isopropanol (40 ml) and N-cyanodiphenoxyimidocarbonate (4.76 g, 0.02 mole) added. After stirring at room temperature for 30 minutes the white precipitate was collected and washed with 15 ml. of isopropanol then dried to yield N-(2-aminophenyl)-N'-cyano-O-phenylisourea, 4.42 g. (88%) mp 234°–235° (d). Ir (nujol): 2200 cm$^{-1}$ (C≡N). $^1$H nmr (DMSO d$_6$): δ 6.5–7.5 (M, aromatics).

$C_{14}H_{12}N_4O$

Anal. Calcd: C, 66.65; H, 4.79; N, 22.21; M+252 Found: C, 66.99; H, 4.71; N, 21.98; M+252.

EXAMPLE 2

A suspension of N-cyanodiphenoxyimidocarbonate (4.76 g., 0.02 mole) and phenylenediamine (2.16 g., 0.02 mole) in isopropanol (40 ml.) was heated at reflux for 1 hour. The volume was reduced to 10 ml. by evaporation. The precipitate therefrom was separated by filtration, washed with cold isopropanol (5 ml.) and then dried to yield 2.90 g. of 2-cyanamidobenzimidazole, (92%), mp 278° (d).

EXAMPLE 3

4-Chloro-o-phenylenediamine (2.86 g., 0.02 mole) was dissolved in 60 ml. of isopropanol and N-cyanodiphenoxyimidocarbonate (4.76 g., 0.02 mole) added with stirring. After stirring 12 hours, the precipitate was separated by filtration, washed with isopropanol (10 ml.) and dried yielding N-(2-amino-5-chlorophenyl)-N'-cyano-O-phenylisourea, 2.3 g. (80%) mp 265° (d). Ir (nujol): 2200 cm$^1$ (C≡N) $^1$H nmr (DMSO d$_6$): δ 7.0–7.45 (m, aromatics).

$C_{14}H_{11}ClN_4O$

Anal. Calcd: C, 58.58; H, 3.86; N, 19.52; Cl, 12.35; M+287 Found: C, 58.65; H, 3.92; N, 19.45; Cl, 12.42; M+287.

EXAMPLE 4

A mixture of N-cyanodiphenoxyimidocarbonate (4.76 g., 0.02 mole) and 4-chloro-o-phenylenediamine (2.86 g., 0.02 mole) in isopropanol (60 ml.) was heated at reflux for 15 hours. The volume was reduced to 20 ml. and the precipitate collected, washed with acetone (10 ml.), isopropanol (10 ml.) and dried to yield 2-cyanamido-5-chlorobenzimidazole, 3.4 g., (88%) mp >300°. Ir (nujol): 2190 cm$^{-1}$ (C≡N). $^1$H nmr (DMSO d$_6$): δ 7.0–7.3 (m, aromatics).

$C_8H_5ClN_4$

Anal. Calcd: C, 49.89; H, 2.62; N, 18.41; Cl, 29.09; M+192 Found: C, 47.65, H, 2.90; N, 18.25; Cl, 29.29; M+192.

The 2-cyanamidobenzimidazole (1 g.) is dissolved in 50 ml. of hydrochloric acid-methanol. The reaction mixture is heated at reflux for 5 hours to give 5-chloro-2-carbomethoxyaminobenzimidazole.

EXAMPLE 5

A slurry of N-cyanodiphenylimidocarbonate (24.0 g., 0.1 mole) and o-aminophenol (11.0 g., 0.1 mole) in isopropanol (150 ml.) was stirred at room temperature for 1 hour. A small portion of the reaction mixture was evaporated to give N-(2-hydroxyphenyl)-N'-cyano-O-phenylisourea. The remaining solution was filtered. The filtrate was heated at reflux for 10 minutes. The crystalline product which formed on cooling was separated by filtration and dried to yield 2-cyanamidobenzoxazole, 11.8 g., (74%) mp 175°. A sample was recrystallized from acetonitrile, mp 186°–188°. Ir (nujol): 2195 cm$^{-1}$ (C≡N).

$C_8H_5N_3O$

Anal. Calcd: C, 60.38; H, 3.17; N, 26.40; M+159 Found: C, 60.14; H, 3.09; N, 26.65; M+159.

EXAMPLE 6

A mixture of N-cyanodiphenoxyimidocarbonate (2.4 g., 0.01 mole) and 4-propylthio-o-phenylenediamine (1.9 g., 0.01 mole) in ethanol is stirred at ambient temperature for ½ hour. The mixture is filtered to give N-(2-amino-5-propylthiophenyl)-N'-cyano-O-phenylisourea. This compound (2 g.) is heated in methanol at reflux for 6 hours. The reaction mixture is flushed with hydrogen chloride gas and the reflux period extended. Working up the reaction mixture as described above gives 5-propylthio-2-carbomethoxyaminobenzimidazole, a potent anthelmintic.

EXAMPLE 7

Substituting equimolar quantities of 4-cyclohexylthio-o-phenylenediamine, 4-methylsulfinyl-o-phenylenediamine, 4-phenylthio-o-phenylenediamine, 4-phenylsulfinyl-o-phenylenediamine, 4-thienylcarbonyl-o-phenylenediamine, 4-n-butyl-o-phenylenediamine or 4-propoxy-o-phenylenediamine in the procedures above gives: N-(2-amino-5-cyclohexylthiophenyl)-N'-cyano-O-phenylisourea, 5-cyclohexylthio-2-cyanamidobenzimidazole and 5-cyclohexylthio-2-carbomethoxyaminobenzimidizole; N-(2-amino-5-methylsulfinylphenyl)-N'-cyano-O-phenylisourea, 5-methylsulfinyl-2-cyanamidobenzimidazole and 5-methylsulfinyl-2-carbomethoxyaminobenzimidazole; N-(2-amino-5-phenylthiophenyl-N'-cyano-O-phenylisourea, 5-phenylthio-2-cyanamidobenzimidazole and 5-phenylthio-2-carbomethoxyaminobenzimidazole; N-(2-amino-5-phenylsulfinylphenyl)-N'-cyano-O-phenylisourea, 5-phenylsulfinyl-2-cyanamidobenzimidazole and 5-phenylsulfinyl-2-carbomethoxyaminobenzimidazole; N-(2-amino-5-thienylcarbonylphenyl-N'-cyano-O-phenylisourea, 5-thienylcarbonyl-2-cyanamidobenzimidazole and 5-thienylcarbonyl-2-carbomethoxyaminobenzimidazole; N-(2-amino-5-n-butylphenyl)-N'-cyano-O-phenylisourea, 5-n-butyl-2-cyanamidobenzimidazole and 5-n-butyl-2-carbomethoxyaminobenzimidazole; and N-(2-amino-5-propoxyphenyl)-N'-cyano-O-phenylisourea, 5-propoxy-2-cyanamidobenzimidazole and 5-propoxy-2-carbomethoxyaminobenzimidazole, respectively.

EXAMPLE 8

Substituting equimolar quantities of 5-methyl-2-aminophenol, 5-phenoxy-2-aminophenol or 5-propylthio-2-aminophenol in the reactions of Example 5 above gives: N-(2-hydroxy-5-methylphenyl)-N'-cyano-O-phenylisourea, 2-cyanamido-6-methylbenzoxazole and 2-carbomethoxyamino-6-methylbenzoxazole; N-(2-hydroxy-5-phenoxyphenyl)-N'-cyano-O-phenylisourea; N-(2-hydroxy-5-propylthiophenyl-N'-cyano-O-phenylisourea and 2-cyanamido-6-propylthiobenzoxazole, respectively.

What is claimed is:

1. The method of preparing a compound of the formula:

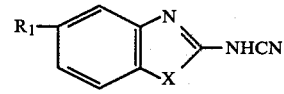

in which X is —O— or —NH— and $R_1$ is hydrogen, halo, acetyl, lower alkyl, lower alkoxy, lower alkylthio, lower alkyl sulfinyl, phenylthio, phenyloxy, phenylsulfinyl, cyclohexylthio, cyclohexyloxy, cyclohexylsulfinyl or thienylcarbonyl, said lower alkyl and lower alkoxy groups having 1–6 carbons, comprising reacting N-cyanodiphenoxyiminocarbonate with a compound of the formula:

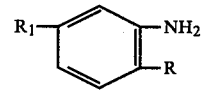

in which R is hydroxy or amino and $R_1$ is as defined above in an organic solvent in which the reactants are soluble at reflux temperature until reaction is complete.

2. The method of claim 1 in which the temperature of reaction is from 80°–100°.

* * * * *